US010045772B2

(12) United States Patent
Hart et al.

(10) Patent No.: US 10,045,772 B2
(45) Date of Patent: Aug. 14, 2018

(54) BONE ANCHOR ASSEMBLY

(71) Applicant: KARL STORZ GmbH & Co. KG, Tuttlingen (DE)

(72) Inventors: Rickey Hart, Marco Island, FL (US); Patrick Hunt, Weisendorf (DE)

(73) Assignee: KARL STORZ & Co. KG, Tuttlingen (DE)

( * ) Notice: Subject to any disclaimer, the term of this patent is extended or adjusted under 35 U.S.C. 154(b) by 167 days.

(21) Appl. No.: 14/846,322

(22) Filed: Sep. 4, 2015

(65) Prior Publication Data
US 2017/0065273 A1 Mar. 9, 2017

(51) Int. Cl.
A61B 17/04 (2006.01)
A61F 2/08 (2006.01)
A61B 90/00 (2016.01)

(52) U.S. Cl.
CPC .... *A61B 17/0401* (2013.01); *A61B 2017/044* (2013.01); *A61B 2017/0408* (2013.01); *A61B 2017/0409* (2013.01); *A61B 2017/0414* (2013.01); *A61B 2017/0424* (2013.01); *A61B 2017/0425* (2013.01); *A61B 2017/0448* (2013.01); *A61B 2017/0453* (2013.01); *A61B 2017/0458* (2013.01); *A61B 2090/031* (2016.02); *A61B 2090/037* (2016.02); *A61F 2/0811* (2013.01)

(58) Field of Classification Search
CPC ........ A61B 17/0401; A61B 2017/0409; A61B 2017/044; A61B 2017/0448; A61B 2017/0453; A61F 2/0811
See application file for complete search history.

(56) References Cited

U.S. PATENT DOCUMENTS

| 5,411,523 | A | 5/1995 | Goble |
| 5,443,467 | A | 8/1995 | Biedermann et al. |
| 5,643,320 | A * | 7/1997 | Lower ................ A61B 17/0401 606/104 |
| 6,656,183 | B2 | 12/2003 | Colleran et al. |
| 7,517,357 | B2 | 4/2009 | Abrams et al. |
| 8,137,389 | B2 | 3/2012 | Biedermann et al. |
| 2007/0203498 | A1 | 8/2007 | Gerber et al. |
| 2009/0112270 | A1 | 4/2009 | Lunn et al. |
| 2009/0312794 | A1 | 12/2009 | Nason et al. |

(Continued)

FOREIGN PATENT DOCUMENTS

| DE | 43 07 576 C1 | 4/1994 |
| DE | 20 2005 022 017 U1 | 7/2012 |

(Continued)

OTHER PUBLICATIONS

Extended European Search Report for European Application No. 16001865.1 dated Jan. 30, 2017.

(Continued)

*Primary Examiner* — Diane Yabut
(74) *Attorney, Agent, or Firm* — Muncy, Geissler, Olds & Lowe, P.C.

(57) ABSTRACT

A suture anchor including a sleeve with an optional solid tip and a threaded, hollow interior portion. A transverse hole passes through a distal end of the sleeve. An inner screw with a flat distal end and threads disposed on an outer surface and a driver head extension monolithically connected with a proximal end of the inner screw are also provided.

20 Claims, 3 Drawing Sheets

(56) References Cited

U.S. PATENT DOCUMENTS

| | | | |
|---|---|---|---|
| 2010/0292732 A1* | 11/2010 | Hirotsuka | A61B 17/0401 606/232 |
| 2010/0318125 A1 | 12/2010 | Gerber et al. | |
| 2013/0060280 A1* | 3/2013 | Wolf | A61B 17/0401 606/232 |
| 2013/0204298 A1 | 8/2013 | Graul et al. | |

FOREIGN PATENT DOCUMENTS

| | | |
|---|---|---|
| EP | 2 292 148 B1 | 8/2011 |
| WO | WO 97/29693 A1 | 8/1997 |
| WO | WO 02/38054 A2 | 5/2002 |
| WO | WO 2009/146155 A1 | 12/2009 |

OTHER PUBLICATIONS

Argus Eiektrotechnik, "Kentaktschrauben, Technische Information," pp. 1-12 (Aug. 2008).

* cited by examiner

BONE ANCHOR ASSEMBLY

BACKGROUND OF THE INVENTION

Field of the Invention

The invention relates to anchoring devices and, in particular, to bone anchors for attaching tissue to bone and a method for using the same.

Description of the Background Art

In the medical and surgical fields, it is sometimes necessary to perform procedures to reattach soft tissue to bone. Soft tissue, such as a tendon or ligament, may rupture, become damaged, or detach from a patient's bone as a result of injury or a medical procedure. Injuries of this type include, torn rotator cuffs, labral tears, bicep tendon tears and quadricep ruptures. Surgical treatment of a torn rotator is designed to reattach the damaged tendon(s) back to the humeral head (ball of the shoulder joint) from which it was torn. Other torn tendons and ligaments require similar procedures.

Bone anchors are one medical implant than can be used to attach soft-tissue to the bone. These anchors are designed to hold the tissue onto the bone at its point of reattachment to allow the tissue to heal and naturally reattach itself to the bone. Typically, the anchor is implanted into a bore or tunnel predrilled into a bone mass and the tendon or ligament is reconnected to the bone with a suture that is attached to the anchor. With advances in arthroscopic surgery, the use of suture anchors has become more popular because of the ease and speed of their use and because of the decreased surgical exposure and morbidity.

Suture anchors provide a stable connection point on the bone for one or more sutures. The sutures themselves tie onto the soft tissue that is being reattached. This combination allows for a firm but flexible bond between the bone and the soft tissue while the natural bond reforms on the bone head.

The implanted suture anchors remain in the bone after the tendon or ligament is fully healed. However, in the event of a false application during the surgical procedure, the anchor must be removable. As a result, it is important that the anchors themselves are both a durable fastener and easily removable. Additionally, anchors should be flush with the bone structure when completely installed to avoid any future irritation.

In prior anchor systems, known in particular from US Patent Publication 2009/0312794 A1, the anchor element is designed such that it has an approximately cylindrical body on whose outer face there are projections that prevent removal of the anchor element after it has been inserted into the bone. These projections can be designed as barb-like elements, for example if the anchor element is driven into the bone, or they can also be designed as an outer thread if the anchor element is turned into the bone in the manner of a screw. The suture is threaded through the transverse bore extending through the body, and the two suture ends are placed in outer longitudinal grooves on the body and guided in the proximal direction. A device called a driver is engaged on the proximal end of the anchor element, and it is usually mounted onto the proximal end of the anchor element. The two suture ends are guided along the driver device and are wound there onto radially projecting stubs for the driving-in procedure.

After the anchor element has been driven into the bone and the driver device has been removed, the two free suture ends are used to secure the detached tissue. To do so, the two suture ends are knotted onto the detached tissue, for example a tendon, lying closely on the bone. The anchor element anchored in the bone, and the bone itself, form the force/abutment points between which the tissue is fixed.

A disadvantage of this operating technique is that the knotting requires considerable experience and dexterity on the part of the operating surgeon. Such knots can come undone, or soft-tissue bridges can form around the knot because the knot is arranged on the outside of the operating site.

Subsequently, so-called knotless anchors were developed, which are known for example from U.S. Pat. No. 7,517,357. This anchor element has a body on whose outer face there are projections that prevent removal of the anchor element inserted in the bone. A transverse bore is arranged in the distal end area of the body and extends through the latter. A suture is threaded transversely through the body. A clamp element is provided which is moveable along the body and is used to clamp the suture. The clamp element is designed as an outer axially moveable sleeve.

In this system, the suture is first threaded through the anchor element. One of the free suture ends is pushed, mostly with the aid of a needle, through the tissue to be fixed, and the pushed-through end is then threaded back in the opposite direction through the transverse bore in the anchor element. The connection between the anchor element and the tissue to be fixed takes the form of a suture loop. The anchor element can now be introduced into the bone, together with the suture after which the free suture ends are pulled so that the protruding loop of the suture, connected to the tissue, is drawn toward the fixing location.

The relative position between the suture and tissue connected to it, and the anchor element is now fixed not by forming a knot, but instead by moving a clamp element through which the suture is fixed or as it were clamped in a defined position on the anchor element. In this way, the loop holding the tissue is also fixed. The protruding free ends can then be cut off, for example, and there is no need to apply a knot.

In the knotless anchor, the clamp element is designed as a sleeve which is mounted on the outside of the body of the anchor element. The sleeve and body are displaceable relative to one another.

In one position of displacement of the sleeve, the suture threaded through the body is freely movable, for example so that the tissue pierced by the suture can be drawn onto the bone and fixed in its position. The sleeve is then moved in order to clamp the suture and fix it in its relative position.

As can be seen in particular from moving from FIG. 4 to FIG. 5 of U.S. Pat. No. 7,517,357, there are several relatively sharp-edged clamp points between which the suture is squeezed. This results in relatively high shearing forces, which means that damage to the suture, and therefore tearing-off of the suture, cannot reliably be ruled out.

In addition, the outer sleeve is a very complicated structural part which, in order to exert a clamping force, has to be slightly spread open by the anchor element. For this purpose, suitable lock-type bridges are needed between the outer face of the body of the anchor element and the inner face of the sleeve, which make release from this locked position difficult or impossible. For this reason, corrective measures, for example during temporary release of the clamping connection, can only be carried out with difficulty, if at all.

It should be borne in mind that the dimensions of such clamp elements are on the order of several centimeters with diameters of several millimeters. Therefore, not only is the production of such parts extremely complex, their handling is also very difficult and, in particular, their stability in respect of the holding or fixing force is extremely problematic.

If a tendon subjected to high loading, for example a tendon from the shoulder area or the knee area, is fixed, it is evident that considerable tensile forces from the tendon act on the assembled structure introduced into the bone and composed of body, clamp element and clamped suture.

If one considers the aforementioned dimensions, it will be evident that the wall thickness of the outer sleeve may at best be in the range of fractions of millimeters, although it is this structural part that is intended to provide the clamping force for holding the suture.

Since the sleeve, because of its construction, covers a certain proportion of the outer face of the body of the anchor element, but this anchor element also serves to hold the whole assembly in the bone via the projections present on its outer face, suitable structural measures have to be taken to ensure that the body of the anchor element as such can in fact be safely anchored in the bone.

Because of the variability of bone strength between people and the numerous locations in which the anchor may be implanted, the anchor may also require expandability to lock it into softer bone tissue. Depending on the application, the whole shaft may need to expand for a complete lock, whereas in other instances only the distal end needs to expand.

In addition, torque from a driver must be carefully applied to ensure that the sleeve and inner screw do not strip and lock irreversibly or over-expand and break. The head of the inner screw, the threads of the inner screw, and the thin walls of the sleeve are all susceptible to damage from over application of torque. Furthermore, the suture and surrounding bone tissue can be damaged if torque is applied after the inner screw has been fully inserted.

SUMMARY OF INVENTION

It is therefore an object of the present invention to provide a bone anchor that improves on the conventional art. Specifically, in an embodiment of the invention a bone anchor assembly is provided that has a knotless configuration which does not shear the suture threaded through the transverse hole. Additionally, several torque limiting features are provided which prevent over-driving of the inner screw. Furthermore, the outer sleeve can be expandable in a number of ways and the driving head can be shorn off leaving the anchor flush with the bone.

Furthermore, according to an exemplary embodiment, the bone anchor includes two pieces an outer sleeve with lateral extensions to grip the bone and an inner screw which is inserted into the sleeve. The inner screw optionally having a square driving head and a predetermined breaking point provided above the threads. The portion of the body just below the breaking point being square in shape so that the screw is still removable after breaking.

According to an exemplary embodiment, the bone anchor is provided with several fail-safes which are not present in conventional bone anchors. For instance, the bone anchor is provided with a predetermined breaking point on the inner screw which breaks at a predetermined torque level. Preferably, this predetermined torque level corresponds to a threshold of torque which may damage the bone anchor. Additionally, the bone anchor is provided with an eyelet just above the solid tip portion. This arrangement prevents the suture inserted into the eyelet from being inadvertently cut by the screw threads and ensures smooth driving of the inner screw even if multiple sutures are being anchored.

According to an exemplary embodiment, the suture anchor could include a sleeve with a solid tip and a threaded, hollow interior portion, a transverse hole passing through a distal end of the sleeve, an inner screw with a flat distal end and threads disposed on an outer surface and a driver head extension monolithically connected with a proximal end of the inner screw. The sleeve additionally being provided with a plurality of slits on the proximal end, or more specifically, four slits and a series of radial projections on an outer surface.

Additionally, according to an exemplary embodiment, the inner screw can have a wider portion near the proximal end between the threads and the driver head extension and the driver head extension includes a square head of the same cross-section as the inner screw body. Furthermore, the interface between the inner screw and the driver head extension can be undercut to provide a predetermined breaking point. Additionally, the suture anchor, or a portion of the suture anchor, can be composed of a bio-absorbable material.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, wherein.

DETAILED DESCRIPTION

Figure 1:
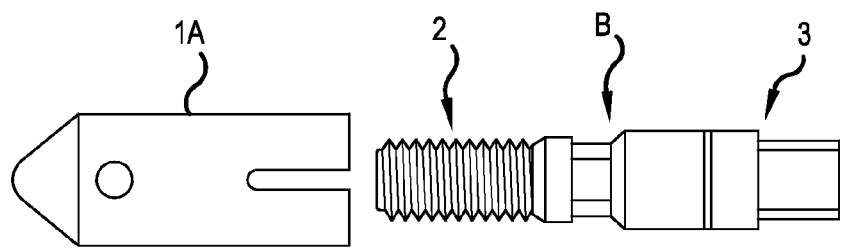
FIG. 1 shows an exploded view of the anchor before insertion of the inner screw.

The exemplary suture anchor of FIG. 1 includes an inner screw 2 which is integrally connected to a square-shaped driver extension 3 and an anchoring sleeve 1A. In describing the suture anchor assembly, the term "distal" refers to the direction in which the suture anchor is inserted, i.e., towards the interior of the bone, and the term "proximal" refers to a direction away from the bone and towards the surgeon, opposite the distal direction.

The inside of the sleeve 1A is provided with threads or a durable material which engage the threads of the inner screw. The sleeve itself contains an eyelet for receiving the suture thread. The sleeve in FIG. 1 is smooth on the outside for application to a pre-drilled hole in the bone. This exemplary embodiment can be applied to very hard bone tissue where expansion of the proximal end is sufficient.

The sleeve 1A can also contain two or more slits beginning at a proximal end and continuing about a on third of the length of the sleeve. This slit allows the sleeve to expand upon complete insertion of the inner screw 2. The distal end of the sleeve beyond the eyelet is solid, providing a surface for the suture to be clamped against.

The anchor assembly can be manufactured from polyether-ether ketone, polylactic acid, lactide, homopolymers and copolymers of glycolide, dioxanone, caprolactone, trimethylene carbonate, and other bio-absorbable and bio-degradable polymers, for example. Alternatively, non-corrosive alloys and metals could be used.

Figure 2:
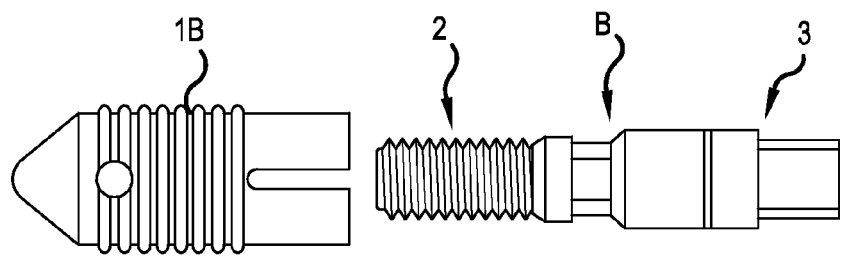
FIG. 2 shows an exploded view of the anchor of a different design before insertion of the inner screw.

Another exemplary design of a sleeve is shown in FIG. 2 with the sleeve 1B having threads disposed on the outer surface. The threads can be replaced by simple projections and barbs for gripping soft tissue or continuous screw-like threads for a tight fit in a pre-drilled hole, for example. The sleeve can thus be changed depending on the operation without altering the rest of the assembly or substantially changing the process of inserting the anchor into the patient. This alternate sleeve can also be provided with a plurality of slits to aid expansion.

The insertion of the bone anchor requires full assembly before it can be inserted into the bone. The inner screw must be fully inserted before the now connected pieces can be screwed into the bone and the suture must be threaded through the eyelet in the sleeve.

Figure 3:
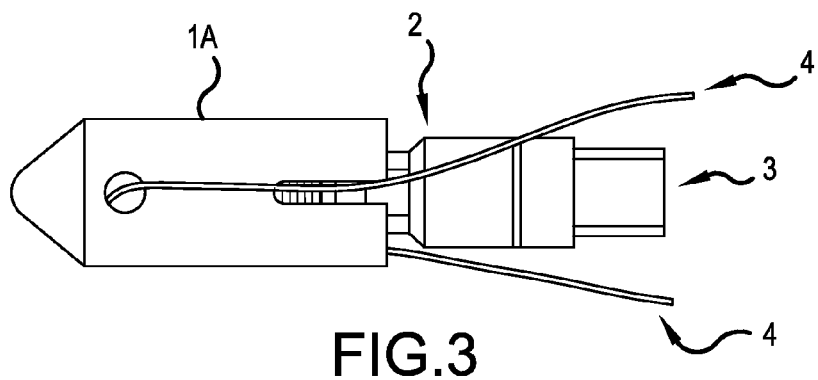
FIG. 3 shows a view of the anchor with suture prior to insertion into the bone.

In FIG. 3 the fully-assembled bone suture anchor is shown with a suture thread 4 in place. The suture thread 4 must be inserted though the eyelet in the sleeve 1A before the inner screw 2 is fully inserted. Once the suture is in place the inner screw 2 can be tightened such that the suture is clamped to the solid distal end of the sleeve.

The driving of the inner screw 2 and the assembly as a whole is accomplished by inserting the square head on the driver extension 3 into a corresponding opening on a driver (not shown). Once the sleeve has been inserted into the bone, the inner screw can be further tightened such that the distal end of the sleeve expands and locks the anchor into the anchoring hole. The proximal end of the inner screw may be provided with a small enlargement, an expanding element, which when fully tightened engages the expandable proximal end of the sleeve and presses it outward.

The suture anchor is configured to receive a plurality of sutures. The number of sutures passing through the eyelet results in a varying depths at which the inner screw will engage the outer sleeve. For example, if four sutures are being clamped then expansion and clamping start at approximately the same time. Alternatively, if only one suture is being clamped, then expansion may begin before the suture is fully clamped.

Figure 4:
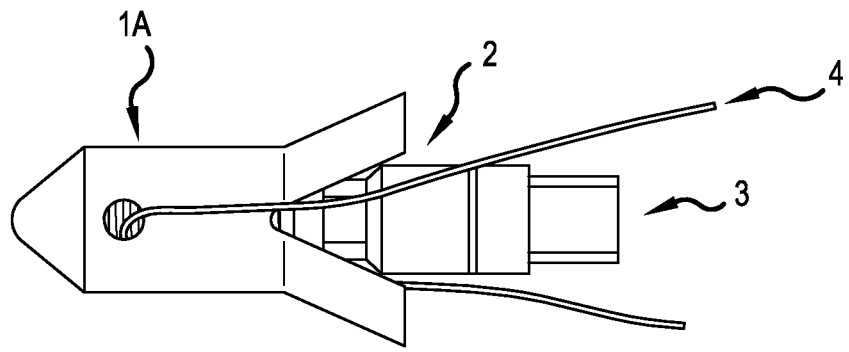
FIG. 4 shows the anchor as it would appear implanted into the bone, but before the screw has been locked in place.

The assembly in FIG. 4 shows how the anchor would appear in situ after the suture anchoring operation has been completed. Additionally, the length of the inner screw and the position of an expanding element on the inner screw are selected such that the expanding element engages and expands the outer sleeve between the slits when a distal end region of the inner screw is engages the suture.

The advantage of this measure is that the clamping and the expanding processes are optimally matched to one another such that the clamping and expanding processes are undertaken simultaneously and in one moving step when the inner screw, on which the expanding element is formed, is moved to the distal end.

The driving of the inner screw should require very little torque since the initial driving through the sleeve is unimpeded. Subsequently, the clamping of the suture and the insertion of the sleeve into the pre-drilled hole in the bone should likewise require little torque. Thus, in normal operation over-driving the inner screw would only result in stripping of the inner threads, or stripping of the driving head, or over-insertion into the pre-drilled hole. All of these scenarios result in the device and the surrounding bone being damaged and perhaps immobilization of the device, preventing correction or removal.

Figure 5:
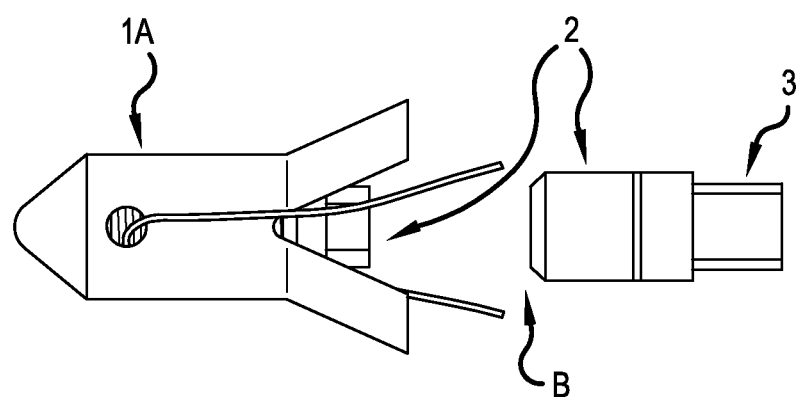
FIG. 5 shows the anchor after being implanted and after the full torque has been applied to lock the screw in place shearing the undercut distal end of the inner screw off.

Therefore, the inner screw 2 and driver head extension 3 are specially adapted to shear or break at a predetermined position B at a predetermined torque limit which would constitute over-driving. This prevents over-driving of the assembly which, because of its small size and precise machining, can be fragile. The drawing of FIG. 5 shows the screw after the torque limit has been reached and the breaking position can be seen neatly dividing the inner screw 2 and the driver head extension 3. The breaking position B can be selected by undercutting or otherwise weakening the screw shaft at this point.

Alternatively, the removable driver head extension can be removed once the operation is completed in the same way it is broken off during torque limiting. Furthermore, the inner screw 2, after separation from the driver head extension 3, still has a square head for additional adjustment or, if necessary, removal of the anchor.

Figure 6:
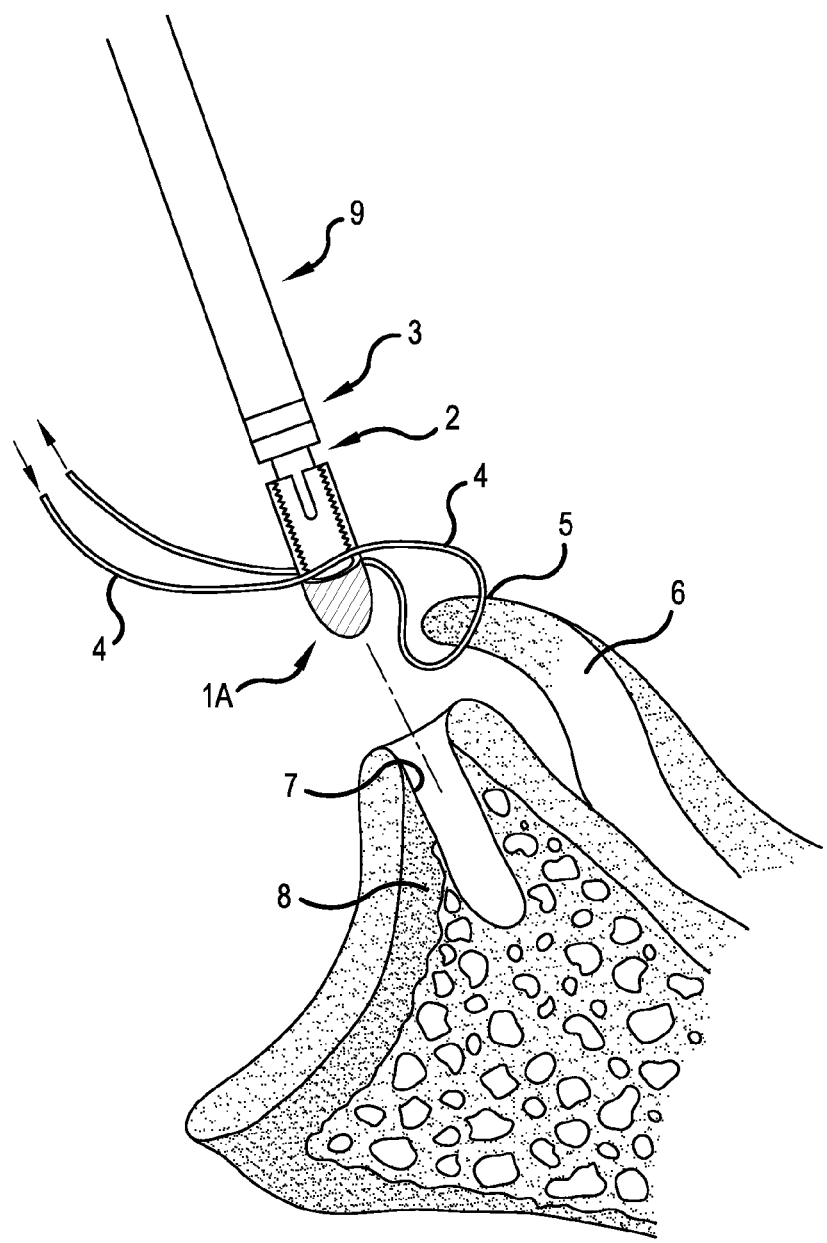
FIG. 6 shows the anchor assembly connected to a driver and suture as part of an arthroscopy.

Finally, the full assembly in operation is shown in FIG. 6. This exemplary procedure is an arthroscopy where a tendon 6 of the rotator cuff is reattached to the shoulder bone 8. The suture 4 is tied through the tendon end 5 and wound back through the anchor. Before the inner screw is completely tightened, the suture length can be adjusted. Subsequently the assembly is inserted into the pre-drilled hole 7 and driver 9 completes the tightening of the inner screw, locking the suture in place within the assembly and expanding the proximal end to secure the bone anchor in the pre-drilled hole.

The invention thus being described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A suture anchor comprising:
   a sleeve with a solid tip and a threaded, hollow interior portion;
   a transverse hole passing through a distal end of the sleeve;
   an inner screw with a flat distal end and threads disposed on an outer surface of the inner screw, wherein after insertion of the inner screw, a proximal end of the inner screw is recessed within the sleeve, the proximal end being axially separated from the threads by a widened portion of the inner screw and a square head of the inner screw; and
   a driver head extension monolithically connected with the proximal end of the inner screw, wherein the driver head extension is configured to break off with a predetermined amount of radial torque at the proximal end of the inner screw such that the driver head extension is separated from the inner screw.

2. The suture anchor of claim 1, wherein the sleeve is provided with a plurality of slits on the proximal end.

3. The suture anchor of claim 2, wherein the number of slits is four.

4. The suture anchor of claim 2, wherein the slits extend radially, entirely through a wall of the sleeve.

5. The suture anchor of claim 1, wherein the transverse hole is provided just above the solid tip of the sleeve.

6. The suture anchor of claim 1, wherein the sleeve has a series of radial projections on an outer surface.

7. The suture anchor of claim 1, wherein the square head is integrally connected to the widened portion of the inner screw.

8. The suture anchor of claim 1, wherein the suture anchor is composed of a bio-absorbable material.

9. The suture anchor of claim 1, further comprising an interface arranged between the inner screw and the driver head extension, the interface being undercut, wherein the driver head extension is configured to break off at the interface with the predetermined amount of torque.

10. The suture anchor of claim 1, wherein the sleeve extends beyond the threads of the inner screw, beyond the widened portion of the inner screw, and beyond the square head of the inner screw, the widened portion being disposed axially in the inner screw between the threads of the inner screw and the square head of the inner screw.

11. The suture anchor of claim 1, wherein the driver head extension is separated from the inner screw at an interface between the square head and the driver head extension.

12. A suture anchor comprising:
a sleeve with a solid tip and a threaded, hollow interior portion;
a transverse hole passing through a distal end of the sleeve;
an inner screw with a flat distal end and threads disposed on an outer surface, wherein the inner screw includes a square head on a proximal end; and
a driver head extension monolithically connected with the proximal end of the inner screw, wherein the driver head extension includes a square head of a same shape and size as the square head of the proximal end of the inner screw,
wherein the driver head extension is configured to separate from the inner screw at an interface at the proximal end of the inner screw and the driver head extension.

13. A suture anchor comprising:
a sleeve with a hollow interior portion;
a transverse hole passing through a distal end of the sleeve;
an inner screw with a flat distal end and threads disposed on the outer surface wherein, after insertion of the inner screw, a proximal end of the inner screw is recessed within the sleeve, the proximal end being axially separated from the threads by a widened portion of the inner screw and a square head of the inner screw; and
a driver head extension monolithically connected with the proximal end of the inner screw,
wherein, after complete insertion of the inner screw, the driver head extension separates from the inner screw leaving the proximal end of the inner screw exposed and recessed within the sleeve, and
wherein a driver connected to the driver head extension also connects to the proximal end of the inner screw after separation of the driver head extension.

14. The suture anchor of claim 13, wherein an interface between the inner screw and the driver head extension is undercut.

15. The suture anchor of claim 14, wherein the driver head extension is configured to break off at the interface with a predetermined amount of torque.

16. The suture anchor of claim 15, wherein the inner screw remains removable after the driver head extension has been broken off.

17. The suture anchor of claim 13, wherein the inner screw has a wider portion sized to engage an expandable portion of the sleeve.

18. The suture anchor of claim 13, wherein a lateral cross-section of the inner screw and the sleeve after insertion has substantially no internal spaces.

19. The suture anchor of claim 13, wherein an intermediate portion of the driver extension head between a square end of the driver head extension and the proximal end of the inner screw is wider than the square end and the proximal end.

20. The suture anchor of claim 19, wherein a driver of the inner screw fits over the square end of the driver head extension and the proximal end of the inner screw.

* * * * *